United States Patent [19]
Brust

[11] Patent Number: 6,030,770
[45] Date of Patent: *Feb. 29, 2000

[54] INCREASING THE SENSITIVITY IN THE IMMUNOCHEMICAL DETERMINATION OF AN ANALYTE

[75] Inventor: Stefan Brust, Marburg, Germany

[73] Assignee: Dade Behring Marburg GmbH, Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/896,056

[22] Filed: Jul. 17, 1997

[30] Foreign Application Priority Data

Jul. 22, 1996 [DE] Germany .............. 196 29 444

[51] Int. Cl.[7] ...................................... C12Q 1/70
[52] U.S. Cl. .............. 435/5; 435/7.1; 435/7.92; 435/7.94; 435/7.95; 435/962; 435/974; 435/975; 436/518; 436/536; 436/538; 436/540
[58] Field of Search ............... 435/5, 7.1, 7.92, 435/7.94, 7.95, 962, 974, 975, 971; 436/518, 536, 538, 540

[56] References Cited

U.S. PATENT DOCUMENTS

| | | | |
|---|---|---|---|
| 4,228,237 | 10/1980 | Hevey et al. ............... | 435/7 |
| 4,376,110 | 3/1983 | David et al. ............... | 436/513 |
| 4,495,296 | 1/1985 | Neurath et al. ............... | 436/530 |
| 4,743,542 | 5/1988 | Graham, Jr. et al. ............... | 435/7 |

FOREIGN PATENT DOCUMENTS

| | | |
|---|---|---|
| 2097545 | 12/1993 | Canada . |
| 0 572 845 | 12/1993 | European Pat. Off. . |
| 572217 | 12/1993 | European Pat. Off. . |

OTHER PUBLICATIONS

Seiichi Hashida et al., "Detection of Antibody IgG to HIV–1 in Urine by Ultrasensitive Enzyme Immunoassay (Immune Complex Transfer Enzyme Immunoassay) Using Recombinant p24 as Antigen for Diagnosis of HIV–1 Infection", Journal of Clinical Laboratory Analysis, pp. 8:86–95, 1994.

*Primary Examiner*—Jeffrey Stucker
*Attorney, Agent, or Firm*—Finnegan, Henderson, Farabow, Garrett & Dunner, L.L.P.

[57] ABSTRACT

The present invention relates to a process for the determination of an analyte, in which a sample optionally containing the analyte to be determined is brought into contact with a first receptor R1, which has a binding affinity for the analyte, immobilized on a solid phase, and a receptor R2, which likewise has a binding affinity for the analyte, is added and in which furthermore the resulting immune complexes are brought into contact with a binding factor which has a binding affinity for the analyte and for a receptor R3 immobilized on the same or a second solid phase and in which the amount of the analyte bound to the first solid phase or, if present, to the second solid phase is detected in a suitable manner.

14 Claims, No Drawings

INCREASING THE SENSITIVITY IN THE IMMUNOCHEMICAL DETERMINATION OF AN ANALYTE

The present invention relates to a process for the determination of an analyte, in which a sample optionally containing the analyte to be determined is brought into contact with a first receptor R1, which has a binding affinity for the analyte, immobilized on a solid phase and a receptor R2, which likewise has a binding affinity for the analyte, is added and in which furthermore the resulting immune complexes are brought into contact with a binding factor which has a binding affinity for the analyte and for a receptor R3 immobilized on the same or a second solid phase and in which the amount of the analyte bound to the first solid phase or, if present, to the second solid phase is detected in a suitable manner.

Customary immunological processes for the diagnosis of illnesses which accompany the formation of specific antibodies against disease-causing agents, such as viruses, bacteria, allergens, autoantigens or against certain medicaments, are based on the capability of the antibodies against form complexes with antigenic structures of the causative agent.

In some of these processes, which are generally described as heterogeneous immunoassays, a sample to be tested for the content of, for example, specific antibody (analyte antibody) is brought into contact with antigenic structures of a disease-causing agent, these antigenic structures being immobilized on suitable, known support materials. Analyte antibodies contained in the sample are bound as an immune complex to the antigenic structures of the disease-causing agent, which are immobilized on the support materials, and detected. For detection, detection antibodies or other specific receptors, such as, for example, protein A, which are capable of complex formation with the analyte antibodies of the sample, are used. The detection reagent generally carries a label which makes the amount of the antibody bound recordable by measuring techniques. Customary labels are, for example: radioactive isotopes, enzymes, fluorescent, phosphorescent or luminescent substances, substances having stable unpaired electrons, erythrocytes, latex particles, magnetic particles and metal sols.

In the case of these processes, both single-stage and multistage detection methods are known. Each process step is customarily concluded with a separation process (washing step). The technique of the single-step method, which is very simple to carry out, in heterogeneous immunoassays, however, is not suitable for the detection of all disease labels. Often, two- or multistage process steps have to be used for technical reasons. Multistage processes are also known which are described as immune complex transfer enzyme immunoassays (S. Hashida et al., Journal of Clinical Laboratory Analysis 8:86–95 (1994)). In these processes, the total immune complex consisting of solid-phase antigen, specific antibody and labeled conjugate antigen is detached from the solid phase. After transferring by pipette to an antibody-binding solid phase, the total immune complex is attached and detected.

These methods are very specific, but have the disadvantage that the disease-causing agents to be detected or antibodies directed against them which have entered in the first step into a complex with the immobilized, specific receptor, can partially be released again from the complex in the following reaction steps in a back-reaction known to the person skilled in the art and thus escape from the detection reaction, as a result of which, inter alia, the sensitivity is greatly restricted. The diagnostic efficiency of such multistage processes is particularly especially restricted if the back-reaction rate between immobilized receptor and the agent to be detected is high. This is the case, for example, with low-affinity antibodies against disease-causing agents or medicaments. These effects are particularly known to the person skilled in the art in processes for the detection of frequently mutating disease-causing agents or disease labels which have a low interaction with the immobilized specific receptor after mutation.

It has already been disclosed in EP 0 572 845 that the back-reaction rate is considerably reduced by addition of a further binding factor for structural features of the agent to be detected. This further binding factor must have more than one site capable of binding to the agent to be detected and must not interfere with the immunochemical detection of the agent. Despite markedly reduced back-reaction, however, even this method does not make it possible to detect specific low-affinity antibodies against disease-causing agents or medicaments safely and with high sensitivity.

The present invention was therefore based on the object of finding reagents which do not have these disadvantages.

It has been found that after completion of the incubation of the immune complex, already formed in the first incubation step, of immobilized specific binding component R1 and analytes having a bioaffinity interaction with it with a specific binding component R2 directed against this analyte, which is generally labeled, a high amount of immune complex of analyte and R2 is to be found in solution. This amount can indeed be reduced, as described in EP-0 572 845, by addition of a receptor which has more than one site capable of binding to the analyte, by attachment to the solid phase, but in some samples still exceeds the amount of immobilized immune complex. Surprisingly, it has been found, however, that by addition of a binding factor and immobilization of a further receptor R3 on the solid phase, the binding factor having an affinity for the analyte and for the receptor R3, the contents of nonimmobilized immune complex of analyte, R2 and binding factor is further decreased. Since R2 generally carries the label, the signal yield is markedly raised and thus the sensitivity of the assay for the analyte is increased. It has moreover been found that after transferring the nonimmobilized portion of the immune complex of analyte, R2 and binding factor to a second solid phase essentially coated with the receptor R3, a very sensitive and specific assay can be carried out.

In contrast to the receptor called a "binding factor" according to EP-0 572 845, the binding factor according to the present invention only needs one site capable of binding to the analyte. An analyte in the sense of the present invention can be either an antibody which has been induced, for example, by a disease-causing agent, or an antigen, such as, for example, the disease-causing agent itself.

The present invention therefore relates to:
a) processes for the determination of an analyte, in which
 (1) a sample optionally containing the analyte to be determined is brought into contact with a first receptor R1, which has a binding affinity for the analyte, immobilized on a solid phase, and a receptor R2, which likewise has a binding affinity for the analyte, is added, which comprises bringing the resulting immune complexes into contact with a binding factor which has a binding affinity for the analyte and for a receptor R3 immobilized on the same or a second solid phase, but no binding affinity for the immobilized receptor R1 and is not labeled and (2) the amount of the analyte bound to the first solid phase or, if present, to the second solid phase is detected in a suitable manner.

b) A process as in a, wherein the receptors R1 and R3 are immobilized on the same solid phase and wherein R3 does not enter into a bioaffinity interaction with the analyte or R2.

c) A process as in a, wherein the receptors R1 and R3 are immobilized on various solid phases and wherein the immune complexes not immobilized on the first solid phase, resulting after bringing together receptor R1, analyte, receptor R2 and binding factor, are brought into contact with the second solid phase.

d) A process as in c, wherein a solution containing the nonimmobilized immune complexes is separated off from the first solid phase and transferred to the second solid phase, which is spatially separate from the first solid phase.

e) A process as in a, wherein the analyte or the receptor R2 carries a detectable label.

f) A process as in e, wherein the receptor R2 is directly or indirectly labeled.

g) A process as in a, wherein the analyte is an antigen.

h) A process as in a, wherein the analyte is an antibody.

i) A process as in a, wherein the binding factor is a conjugate which contains an antibody or an antibody fragment and a further structural element, the antibody or the antibody fragment having a binding affinity for one structural element and the further structural element having a binding affinity for the other element, selected from the group of the element analyte and receptor R3.

k) A process as in i, wherein the binding factor is a biotinylated antibody and the receptor R3 is an antibody directed against biotin.

l) A process as in i, wherein the binding factor is a biotinylated antibody and the receptor R3 is avidin or streptavidin.

m) A process as in a for the detection of antibodies against human immunodeficiency virus (HIV).

n) A test kit for use in a process as in b, which comprises a solid phase having the receptors R1 and R3 immobilized thereon, and the binding factor in solubilized for solubilizable form.

o) A test kit for use in a process as in c, which comprises a first solid phase having receptor R1 immobilized thereon, a second solid phase having receptor R3 immobilized thereon and the binding factor in solubilized or solubilizable form.

That the binding factor is not labeled means in the sense of the present invention that it either carries no label or at least not the same label with which the extent of the binding of the analyte to the first or second phase is determined.

Processes in which the immobilized receptors R3 can be used are known to the person skilled in the art in all their embodiments. It is important that the processes according to the invention can be employed in suitable form in all immunochemical processes in which in a first step an immunochemical or comparable binding of an analyte to a preferably immobilized, specific receptor takes place and in a second, but not necessarily chronologically separate step, a direct or indirect detection takes place. The processes according to the invention are preferably employed in the processes known to the person skilled in the art as sandwich ELISAs, an enzyme preferably being used as a labeling system, preferably with a chromogenic or fluorogenic substrate or a chemoluminescent label as a labeling system. The embodiment selected, however, does not in principle affect the use possibilities of the processes according to the invention.

Solid phases used are preferably microtiter plates, magnetic particles, latex particles or matrix-chemical test elements, such as, for example, test modules comprising fibers or membranes.

It is known to the person skilled in the art that immunochemical processes, as described above, can be employed for the simultaneous determination of different analytes, such as, for example, HIV 1, HIV 2 or HCV, and of antibodies directed against these analytes. Such embodiments are hereby expressly included.

Binding factors in the sense of the present invention are specific receptors which have one or more than one bioaffinity binding site for R2. Furthermore, they undergo an interaction with the receptor R3. Binding components or components of the binding factors can be antibodies, antibody fragments or conjugates comprising antibodies or antibody fragments and a further component, such as, for example, an enzyme. These antibodies or antibody fragments or conjugates thereof can be directed against the analyte or else also against the analyte and R3. The binding factor can also consist of an antibody or antibody fragment which is coupled to a structural element against which the receptor R3 is directed.

Receptors R3 in the sense of the present invention are specific binding components which have one or more than one bioaffinity binding site for the binding factor. Receptors R3 or components of this binding component can be antibodies, antibody fragments or conjugates comprising antibodies or antibody fragments and a further component, such as, for example, an enzyme. These antibodies or antibody fragments and conjugates thereof can be directed against the binding factor or else contain antigenic structures which are recognized by binding sites of the binding factor. Receptor R3 can also consist of a protein which is coupled to a structural element against which the binding factor is directed.

Preferred combination of binding components for the specific detection of antigens:

R1: antibody immobilized on a solid phase, which is directed against the analyte, Analyte: antigen, R2: antibody provided with a label (=conjugate antibody), which is directed against the analyte Binding factor: antibody which is directed against the analyte, R3: antibody immobilized on the solid phase, which is directed against the binding factor.

In the case of antigen detection, preferably an antibody or an antibody fragment is used as a binding factor, which does not recognize the same epitope as the solid-phase antibody R1 or the conjugate antibody R2.

Preferred combination of binding components for the detection of specific antibodies:

R1: antigen immobilized on a solid phase, against which the analyte is directed, Analyte: antibody, R2: antigen provided with a label, which is directed against the analyte, Binding factor: antibody which is directed against the analyte, R3: antibody immobilized on the solid phase, which is directed against the binding factor.

Particularly preferred combination of binding components for the detection of specific antibodies:

R1: antigen immobilized on a solid phase, against which the analyte is directed, Analyte: antibody, R2: antigen provided with a label, against which the analyte is directed, Binding factor: antibody which is directed against the analyte and carries additional, nonantibody-endogenous epitopes, R3: antibody immobilized on the solid phase, which is directed against the additional, nonantibody-endogenous epitope of the binding factor.

Methods for the preparation of conjugates which consist of an antibody and an additional, nonantibody-endogenous antigen (for example biotin) are known to the person skilled in the art. Such conjugates can be prepared, for example, by linking by means of chemical reagents or by bioaffinity interaction, retaining the bioaffinity function of their starting materials. Hybrid molecules can also be produced by chemical synthesis, the hybridoma technique or genetic engineering methods.

The reagent according to the invention can be employed in a multiplicity of processes of human and veterinary diagnosis. Examples which should be mentioned are: two- or multistage tests for detection of antibodies of various immunoglobulin classes against structural features of viruses (e.g. hepatitis A, B and C viruses, and various HIV types) and processes for detection of bacterial and parasitic causative organisms and of allergic diseases. Further examples are the detection of disease-causing agents, such as viruses, (e.g. hepatitis B virus), bacteria, parasites and allergens, and also of markers of diseases (e.g. tumor markers) in single- and multistage detection processes.

The invention is additionally illustrated by the following examples which, however, are in no way to be understood as being restrictive.

EXAMPLE 1 a) Preparation of the Solid Phase

Microtiter plates type B (Nunc, Roskilde, Denmark) are incubated at 4° C. for 24 hours with 100 µl per well of coating solution (600 µg/ml of recombinant gp41 [Behringwerke AG, Marburg, FRG] and 10 mg/ml of monoclonal antibody against biotin [Behringwerke AG, Marburg, FRG] in 50 mM sodium carbonate buffer, pH 9.5). The wells of the microtiter plates are then washed three times with 300 µl each of wash solution (50 mM tris, 0.1% Tween 20, pH 7.2). The microtiter plates dried over silica gel are stable for 1 year with exclusion of air.

b) Preparation of the Conjugate 10 mg of HIV 1-gp41 peptide (IAF Biochem, Laval, Canada) are dissolved in 1 ml of glacial acetic acid/water (50:50, v/v). After neutralizing with 5N sodium hydroxide solution, the mixture is treated with a 10-fold molar excess of N-γ-maleimidobutyrylsuccinimide and incubated at room temperature for 1 hour. The unreacted hetero-bifunctional reagent is separated by gel filtration (Sephadex G-25) using 100 mM sodium phosphate, 5 mM nitrilotriacetic acid, pH 6.0.

10 mg of horseradish peroxidase (Boehringer Mannheim, Mannheim, FRG) are incubated at room temperature for 1 hour with a 100-fold molar excess of 2-iminothiolane in 10 ml of 10 mM sodium phosphate, 100 mM sodium chloride, pH 8.0. Free modification reagent is then removed by gel filtration (Sephadex G-25) using 100 mM sodium phosphate, 5 mM nitrilotriacetic acid, pH 6.0. Both eluates (SH-activated peroxidase and maleimide-modified HIV 1 peptide) are combined and incubated at room temperature overnight. After stopping the reaction with 1/10 vol of 100 mM N-ethylmaleimide, the conjugate is purified from unreacted HIV 1 peptide by gel filtration (Sephadex G-25). After concentrating (2 mg/ml), the conjugate is stored at −20° C.

c) 2-step Enzyme Immunoassay for the Detection of HIV 1 Antibodies

An enzyme immunoassay for the detection of anti-HIV 1 is carried out as follows:

25 µl of sample buffer (0.3 M tris/HCl, 1% albumin, 2% Tween 20, pH 7.2) are incubated at 37° C. for 30 minutes with 100 µl of human serum in the wells of the microtiter plates prepared according to Example 1a. After washing 4 times with 50 mM PBS, 0.1% Tween 20, 100 µl of the conjugate prepared according to Example 1b (1:1,000 in 0.1 M tris/HCl, 1% albumin, 2% Pluronic F64, pH 8.1) are pipetted in. The 30-minute incubation (+37° C.) is ended with 4 further washing steps. The bound peroxidase activity, which correlates directly with the number of bound anti-HIV 1 antibodies, is determined by addition of $H_2O_2$/tetramethylbenzidine. The substrate conversion is stopped by addition of 0.5 M sulfuric acid after 30 minutes at room temperature. The extinction is determined at 450 nm.

d) Preparation of the Biotinylated Antibody 10 mg of monoclonal antibody against human immunoglobulin G [Behringwerke AG, Marburg, FRG] are incubated at room temperature for 1 hour with a 10-fold molar excess of N-hydroxysuccinimide-X-biotin in 10 mM sodium phosphate, 100 mM sodium chloride, pH 8.0 in 10 ml of 10 mM sodium phosphate, 100 mM sodium chloride, pH 8.0. Free modification reagent is then removed by gel filtration (Sephadex G-25) using 100 mM tris, 5 mM nitrilotriacetic acid, pH 7.0.

e) Use of the Reagent According to the Invention

Anti-HIV 1-positive and anti-HIV-negative sera are investigated in an enzyme immunoassay as in Example 1c (reference system I). Anti-HIV 1-positive samples having an unusually low reactivity are additionally investigated in the assay system according to the invention (system I according to the invention). To do this, a biotinylated anti-human IgG antibody (1 µg/ml) prepared as in Example 1d is additionally added to the conjugate solution according to Example 1c.

As a further reference system, this anti-human IgG antibody without a biotin fragment is added in a concentration of 1 µg/ml to the conjugate of Example 1c (reference system II). The results (extinction units) of the investigation are found in Table 1.

TABLE 1

| Sample I.D. | Anti-HIV status | Dilution | Comments | Reference system I | Reference system II | System I according to the invention |
|---|---|---|---|---|---|---|
| Negative control | Negative | Native | | 0.053 | 0.039 | 0.042 |
| Positive control | Positive | 1:800 | High-affinity | 2.076 | 1.875 | 1.964 |
| 9111/39 | Positive | 1:20 | Low-affinity | 1.059 | 1.827 | 2.276 |
| 9111/41 | Positive | 1:10 | Low-affinity | 0.476 | 0.873 | 1.659 |
| 9111/54 | Positive | 1:20 | Low-affinity | 1.049 | 1.915 | >2.500 |
| 9111/53 | Positive | 1:10 | Low-affinity | 0.407 | 0.952 | 1.947 |
| 9304/11 | Positive | 1:500 | High-affinity | 1.049 | 0.862 | 1.183 |

TABLE 1-continued

| Sample I.D. | Anti-HIV status | Dilution | Comments | Reference system I | Reference system II | System I according to the invention |
|---|---|---|---|---|---|---|
| BS 5 | Negative | Native | | 0.084 | 0.42 | 0.063 |
| BS 54 | Negative | Native | | 0.059 | 0.054 | |
| BS 13 | Negative | Native | | 0.061 | 0.048 | 0.070 |
| BS 15 | Negative | Native | | 0.071 | 0.039 | 0.053 |

Marked differences in the signal formation in the 3 assay systems is particularly to be detected with low-affinity samples (e.g. 9111/53). The sensitivity with respect to these samples is increased by a factor of 4 compared with the reference system I and doubled compared with the reference system II. Samples having a high affinity for the coating antigen, which are safely detected in the reference system I, too, even at high dilution, as well as anti-HIV-negative sera, undergo no signal increase in the system I according to the invention.

EXAMPLE 2
a) Preparation of the Solid Phase

Microtiter plates (Nunc, Roskilde, Denmark, type B) are incubated at 4° C. for 24 hours with 100 µl per well of coating solution (10 mg/ml of rabbit antibody against mouse immunoglobulin [Behringwerke AG, Marburg, FRG] in 50 mM sodium carbonate buffer, pH 9.5). The wells of the microtiter plates are then washed three times with 300 µl each of wash solution (50 mM tris, 0.1% Tween 20, pH 7.2). The microtiter plates dried over silica gel are stable for 1 year with exclusion of air.

b) Transfer Enzyme Immunoassay for the Detection of HIV 1 Antibodies

A transfer enzyme immunoassay for the detection of anti-HIV 1 is carried out as follows: 25 µl of sample buffer (0.3 M tris/HCl, 1% albumin, 2% Tween 20, pH 7.2) are incubated at 37° C. for 30 minutes with 100 µl of human serum in the wells of the microtiter plates prepared according to Example 1a. After washing 4 times with 50 mM PBS, 0.1% Tween 20, 100 µl of the conjugate prepared according to Example 1b (1:1,000 in 0.1 M tris/HCl, 1% albumin, 2% Pluronic F64, pH 8.1) are pipetted in, which conjugate has been made up by additional addition of 1 µg/ml of monoclonal antibody against human immunoglobulin. After incubation for 30 minutes (+37° C.), the solution of the conjugate phase (100 µl) is transferred by pipette to the wells of the microtiter plates prepared according to Example 2a (system II according to the invention). The antigen-coated test plates are further processed as described above and assessed (reference system III). The microtiter plates according to Example 2a which were coated with antibody, and now contain the immune complexes transferred by pipette, are washed four times at 37° C. after incubation for a further 30 minutes. The bound peroxidase activity, which correlates directly with the number of bound anti-HIV 1 antibodies, is determined by addition of $H_2O_2$/tetramethylbenzidine. The substrate conversion is stopped after 30 minutes at room temperature by addition of 0.5 M sulfuric acid. The extinction is determined at 450 nm. The results (extinction units) of the investigation are found in Table 2. The signal difference between the reference system III and the system II according to the invention, in turn in the low-affinity samples, is clearly to be detected therein. In the system II according to the invention, in some cases double the sensitivity is achieved. Samples having high affinity for the coating antigen, which are safely detected in the reference system III, too, even at high dilution, as well as anti-HIV-negative sera, undergo no signal increase in the system II according to the invention.

TABLE 2

| Sample I.D. | Anti-HIV status | Dilution | Comments | Reference system III | System II according to the invention |
|---|---|---|---|---|---|
| Negative control | Negative | Native | | 0.104 | 0.106 |
| Positive control | Positive | 1:800 | High-affinity | 1.868 | 1.274 |
| 9111/39 | Positive | 1:20 | Low-affinity | 1.424 | >2.500 |
| 9111/41 | Positive | 1:10 | Low-affinity | 0.835 | 2.335 |
| 9111/54 | Positive | 1:20 | Low-affinity | 1.679 | >2.500 |
| 9111/53 | Positive | 1:10 | Low-affinity | 0.954 | >2.500 |
| 9304/11 | Positive | 1:500 | High-affinity | 0.868 | 1.334 |
| BS 5 | Negative | Native | | 0.157 | 0.126 |
| BS 54 | Negative | Native | | 0.134 | 0.100 |
| BS 13 | Negative | Native | | 0.128 | 0.099 |
| BS 15 | Negative | Native | | 0.147 | 0.107 |

I claim:

1. A process for the determination of an analyte, wherein said process comprises:
    (1) contacting a sample potentially containing the analyte with:
        (a) first receptor R1, which has a binding affinity for the analyte and which is immobilized on a solid phase, and
        (b) a receptor R2, which has a binding affinity for the analyte;
    (2) contacting the resulting immune complexes with a binding factor which has a binding affinity for the analyte and for a receptor R3 immobilized on the same or a second solid phase, but has no binding affinity for the immobilized receptor R1; and
    (3) detecting the amount of the analyte bound to the first solid phase, or, if present, to the second solid phase.

2. The process as claimed in claim 1, wherein the receptors R1 and R3 are immobilized on the same solid phase and wherein R3 undergoes no bioaffinity interaction with the analyte or R2.

3. The process as claimed in claim 1, wherein the receptors R1 and R3 are immobilized on various solid phases and wherein the immune complexes not immobilized on the first solid phase, resulting after bringing together receptor R1, analyte, receptor R2 and binding factor, are brought into contact with the second solid phase.

4. The process as claimed in claim 3, wherein a solution containing the nonimmobilized immune complexes is separated off from the first solid phase and transferred to the second solid phase, which is spatially separate from the first solid phase.

5. The process as claimed in claim 1, wherein the analyte or the receptor R2 carries a detectable label.

6. The process as claimed in claim 5, wherein the receptor R2 is directly or indirectly labeled.

7. The process as claimed in claim 1, wherein the analyte is an antigen.

8. The process as claimed in claim 1, wherein the analyte is an antibody.

9. The process as claimed in claim 1, wherein the binding factor is a conjugate which contains an antibody or an antibody fragment and a further structural element, the antibody or the antibody fragment having a binding affinity for one structural element and the further structural element having a binding affinity for the other element, selected from the group of the elements analyte and receptor R3.

10. The process as claimed in claim 9, wherein the binding factor is a biotinylated antibody and the receptor R3 is an antibody directed against biotin.

11. The process as claimed in claim 9, wherein the binding factor is a biotinylated antibody and the receptor R3 is avidin or streptavidin.

12. The process as claimed in claim 1 for the detection of antibodies against human immunodeficiency virus (HIV).

13. A test kit for use in a process as claimed in claim 2, which comprises a solid phase having the receptors R1 and R3 immobilized thereon, and the binding factor in solubilized or solubilizable form.

14. A test kit for use in a process as claimed in claim 3, which comprises a first solid phase having a receptor R1 immobilized thereon, a second solid phase having a receptor R3 immobilized thereon and the binding factor in solubilized or solubilizable form.

* * * * *